United States Patent
Hoffman

(10) Patent No.: US 6,873,678 B2
(45) Date of Patent: Mar. 29, 2005

(54) METHODS AND APPARATUS FOR COMPUTED TOMOGRAPHIC CARDIAC OR ORGAN IMAGING

(75) Inventor: David M Hoffman, New Berlin, WI (US)

(73) Assignee: GE Medical Systems Global Technology Company LLC, Waukesha, WI (US)

(*) Notice: Subject to any disclaimer, the term of this patent is extended or adjusted under 35 U.S.C. 154(b) by 0 days.

(21) Appl. No.: 09/750,387

(22) Filed: Dec. 28, 2000

(65) Prior Publication Data
US 2004/0071256 A1 Apr. 15, 2004

(51) Int. Cl.[7] .............................. A61B 6/03; G21K 1/12
(52) U.S. Cl. .................................... 378/19; 250/370.09
(58) Field of Search ................................ 378/4, 9, 145, 378/98.8, 19; 250/370.09, 370.11, 363.04, 367

(56) References Cited

U.S. PATENT DOCUMENTS

| | | | |
|---|---|---|---|
| 3,952,201 A | | 4/1976 | Hounsfield |
| 4,641,328 A | * | 2/1987 | Fujise .............................. 378/8 |
| 5,057,692 A | | 10/1991 | Greskovich et al. |
| 5,400,379 A | * | 3/1995 | Pfoh et al. ..................... 378/19 |
| 5,585,638 A | | 12/1996 | Hoffman |
| 5,799,057 A | * | 8/1998 | Hoffman et al. ............. 378/147 |
| 5,845,003 A | | 12/1998 | Hu et al. |
| 5,974,109 A | * | 10/1999 | Hsieh ........................... 378/19 |
| 5,982,846 A | * | 11/1999 | Toth et al. ..................... 378/19 |
| 6,087,665 A | | 7/2000 | Hoffman et al. |
| 6,115,448 A | | 9/2000 | Hoffman |
| 6,134,301 A | | 10/2000 | Mruzek et al. |
| 6,137,857 A | | 10/2000 | Hoffman et al. |
| 6,144,718 A | | 11/2000 | Hoffman et al. |
| 6,173,031 B1 | | 1/2001 | Hoffman et al. |
| 6,188,745 B1 | * | 2/2001 | Gordon ........................ 378/19 |
| 6,198,791 B1 | | 3/2001 | He et al. |
| 6,259,766 B1 | * | 7/2001 | Cuppen ....................... 378/147 |

FOREIGN PATENT DOCUMENTS

JP  03-259569  * 11/1991  ........... H01L/27/14

* cited by examiner

*Primary Examiner*—Edward J. Glick
*Assistant Examiner*—Chih-Cheng Glen Kao
(74) *Attorney, Agent, or Firm*—Carl B. Horton, Esq.; Armstrong Teasdale LLP

(57) ABSTRACT

One aspect of the present invention is a method for imaging an organ of a patient that includes steps of: scanning a volume of a patient's body including an organ of the patient with a computed tomographic (CT) imaging system having a radiation source and detector coupled to a rotating gantry, the detector array having a z-direction parallel to an axis of rotation of the gantry and an x-direction transverse to the z-direction; acquiring attenuation data from a plurality of staggered half detector segments of the detector array; and reconstructing an image including the patient's organ using the acquired attenuation data.

20 Claims, 5 Drawing Sheets

METHODS AND APPARATUS FOR COMPUTED TOMOGRAPHIC CARDIAC OR ORGAN IMAGING

BACKGROUND OF THE INVENTION

This invention relates generally to methods and apparatus for computed tomographic cardiac imaging systems, and more particularly to methods and apparatus specialized for cardiac imaging with substantial component reuse.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

More particularly, and referring to FIGS. 5 and 6, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In a multislice imaging system 10, detector array 18 comprises a plurality of parallel detector rows, wherein each row comprises a plurality of individual detector elements 20. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

For example, and referring to FIGS. 7 and 8, a multislice detector array 18 includes a plurality of detector modules 50. Each detector module 50 has a plurality of detector elements 20. Particularly, each x-ray detector module 50 includes a plurality of photodiodes 52, a semiconductor device 54, and at least one flexible electrical cable 56. Scintillators 58, as known in the art, are positioned above and adjacent photodiodes 52. Photodiodes 52 may be individual photodiodes or a multidimensional photodiode array. Photodiodes 52 are optically coupled to scintillators 58 and generate electrical outputs on lines 60 representative of light generated by scintillators 58. Each photodiode 52 produces a separate electrical output 60 that is a measurement of the beam attenuation for a specific detector element 20. In one known embodiment, photodiode output lines 60 from each detector module 50 are located at the top and bottom of the photodiode array.

Semiconductor device 54, in one embodiment, includes two semiconductor switches 62 and 64. Switches 62 and 64 each include a plurality of field effect transistors (FETs) (not shown) arranged as a multidimensional array. Each FET includes an input line electrically connected to a photodiode output 60, an output line, and a control line (not shown). FET output and control lines are electrically connected by flexible cable 56. Particularly, one-half of photodiode output lines 60 are electrically connected to each FET input line of switch 62 with the remaining one-half of photodiode output lines 60 electrically connected to FET input lines of switch 64.

Flexible electrical cable 56 includes a first end (not shown), a second end (not shown) and a plurality of electrical wires 66 traveling therebetween. Cable 56 may, for example, be a single cable having multiple first ends 68 and 70 or in another known embodiment, may include multiple cables (not shown) each having a first end (not shown). FET output and control lines are electrically connected to cable 56 by wire bonding. Cable first ends 68 and 70 are secured to detector module 50 using mounting brackets 72 and 74.

Detector modules 50 are secured to detector array 18 using rails 76 and 78.

One known detector array 18 is arcuate. However, and referring to FIG. 9, detector arrays are represented in simplified drawings by a flat, two-dimensional representation of the area exposed to radiation beam 16. In such representations, the axis of rotation of gantry 12 defines a z-direction of detector array 18. A transverse direction, i.e., the direction in which each row of detector elements 20 extends, defines an x-direction. In FIG. 9, rows (not separately shown) of detector elements 20 extend linearly in the plane of the paper, but each row, in reality, follows the arc of detector array 18. Centerline 80 on FIG. 9 represents an imaginary line of a radiation beam 16 passing through an axis of rotation of gantry 12. Detector array 18 is at least approximately symmetric about centerline 80, i.e., it is operationally insignificant if there is a slight asymmetry in the number of detector cells 20 on each side of centerline 80.

FIG. 9 is not drawn to scale. In addition, only a few detector modules 50 are represented in FIG. 9. In one known imaging system, fifty-seven detector modules 50, each having 16 rows of 16 elements, are assembled in detector array 18.

One problem with known imaging systems 10 is that they do not have detector arrays 18 that provide a sufficient number of rows of detector elements 20 to image a heart or other organ of patient 22 in a single revolution of radiation source 14 and detector array 18. Thus, known cardiac CT imaging methods require multiple revolutions and a substantial amount of time (relative to a cardiac cycle).

It would, in principle, be possible to image an entire heart in a single revolution using a larger detector array 18 that had a sufficient number of detector rows to capture attenuation data from all parts of the heart. A CT imaging system 10 having such a detector array 18 would provide the advantage of reducing a patient's total radiation dosage during a cardiac scan. However, to provide acceptable resolution for diagnostic purposes, detector array 18 would have to generate massive amounts of data from a large total number of detector elements. Providing a data acquisition system 32 capable of handling such a large amount of data would be costly.

It is known to selectively combine data from a plurality of adjacent detector rows (i.e., a "macro row") to obtain images representative of slices of different selected thicknesses, which also reduces the amount of data that must be handled by data acquisition system 32 during a scan. If a detector array 18 large enough to image an entire heart during a single revolution were provided, rows could be combined to reduce the amount of data generated. Alternately, detector elements 20 could simply be made larger to provide increased coverage without providing massive amounts of data. However, either of these alternatives runs a significant risk of reducing resolution to unacceptable levels.

It would therefore be desirable to provide methods and apparatus to provide satisfactory CT cardiac imaging with a minimum number of revolutions of an x-ray source and detector. It would further be desirable if such imaging could be accomplished with a single revolution. It would also be desirable to reduce the amount of data collected during such a cardiac CT scan without making unacceptable sacrifices in image quality and resolution.

BRIEF SUMMARY OF THE INVENTION

There is therefore provided, in one embodiment of the present invention, a method for imaging an organ of a patient. The method includes steps of: scanning a volume of a patient's body including an organ of the patient with a computed tomographic (CT) imaging system having a radiation source and detector coupled to a rotating gantry, the detector array having a z-direction parallel to an axis of rotation of the gantry and an x-direction transverse to the z-direction; acquiring attenuation data from a plurality of staggered half detector segments of the detector array; and reconstructing an image including the patient's organ using the acquired attenuation data.

The above-described embodiment is capable of providing satisfactory CT cardiac imaging with a minimum number of revolutions of an x-ray source and detector of the CT imaging system, without unacceptable sacrifices in image quality and resolution.

DETAILED DESCRIPTION OF THE INVENTION

Figure 1:
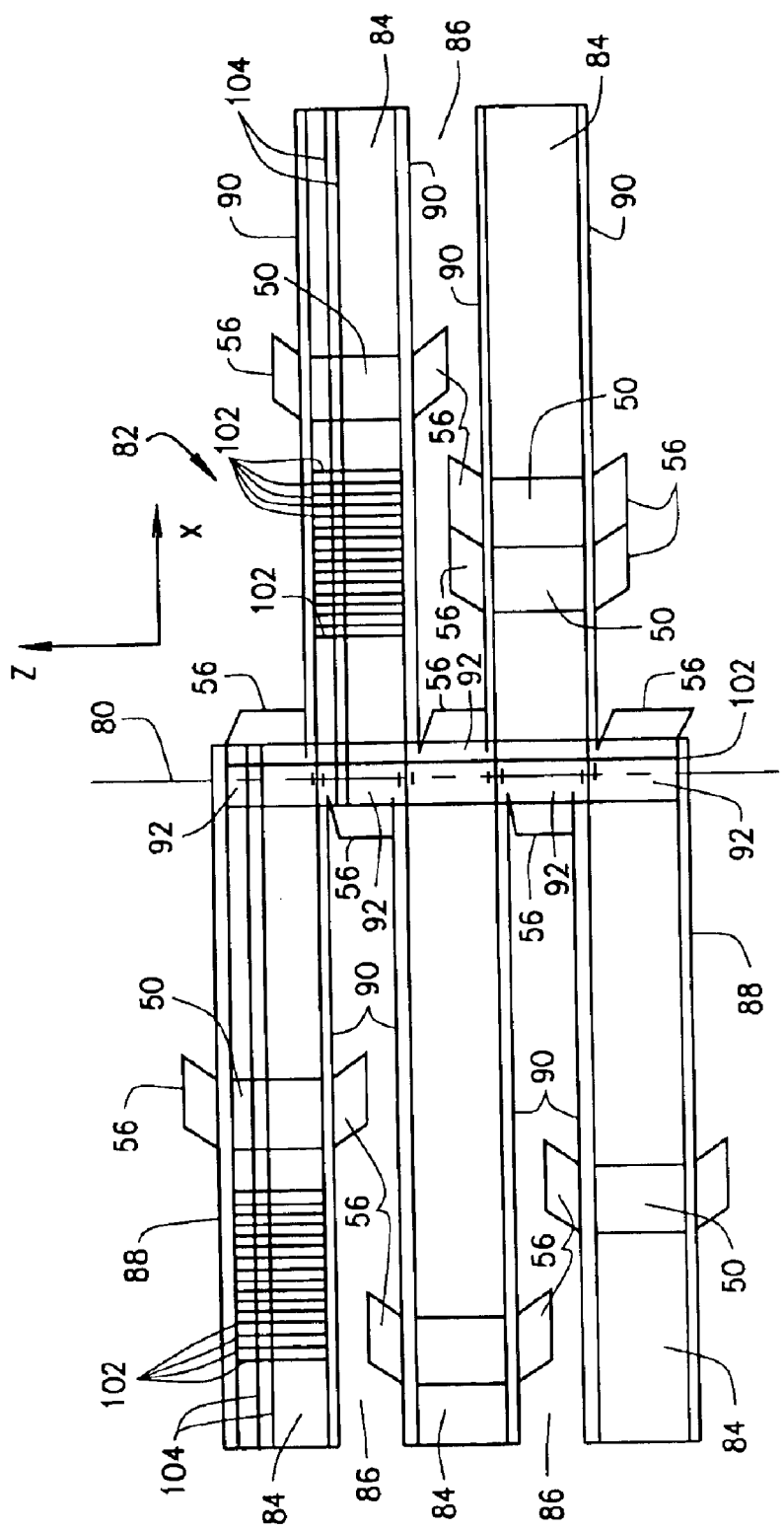
FIG. 1 is a simplified view of an embodiment of a detector array of the present invention as seen looking towards the detector from the x-ray source.
Figure 9:
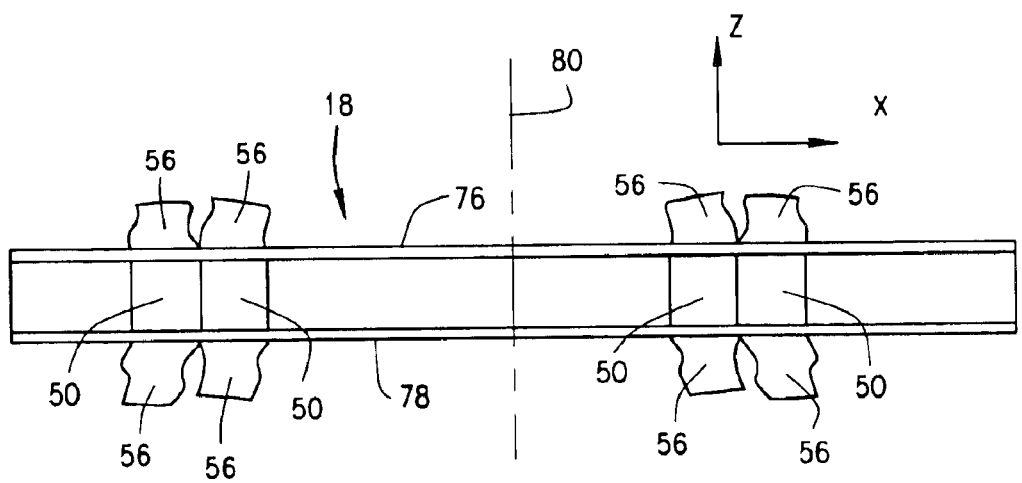
FIG. 9 is a simplified view of the prior art CT system detector array embodiment illustrated in FIG. 7.
Figure 5:
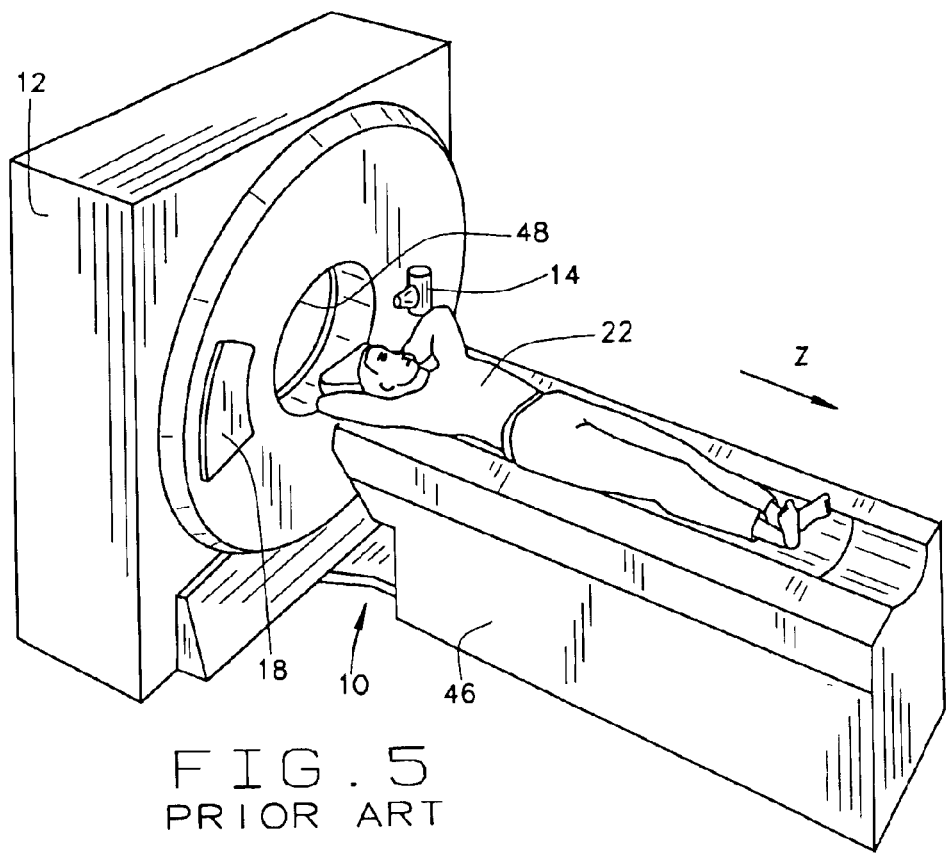
FIG. 5 is a pictorial view of a prior art CT imaging system embodiment.
Figure 6:
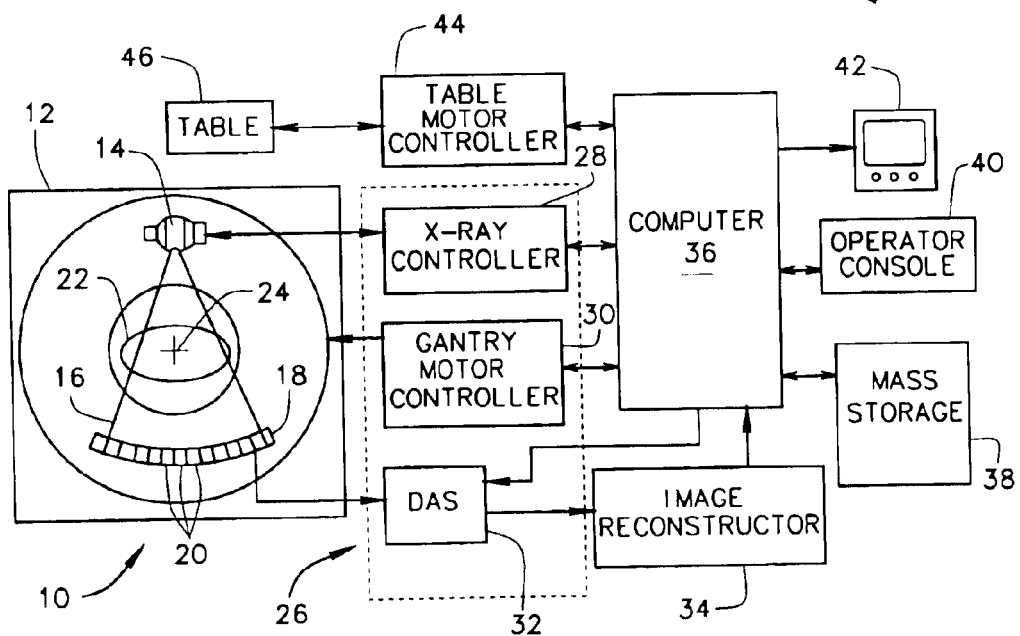
FIG. 6 is a block schematic diagram of the prior art system illustrated in FIG. 1.
Figures 7, 8:
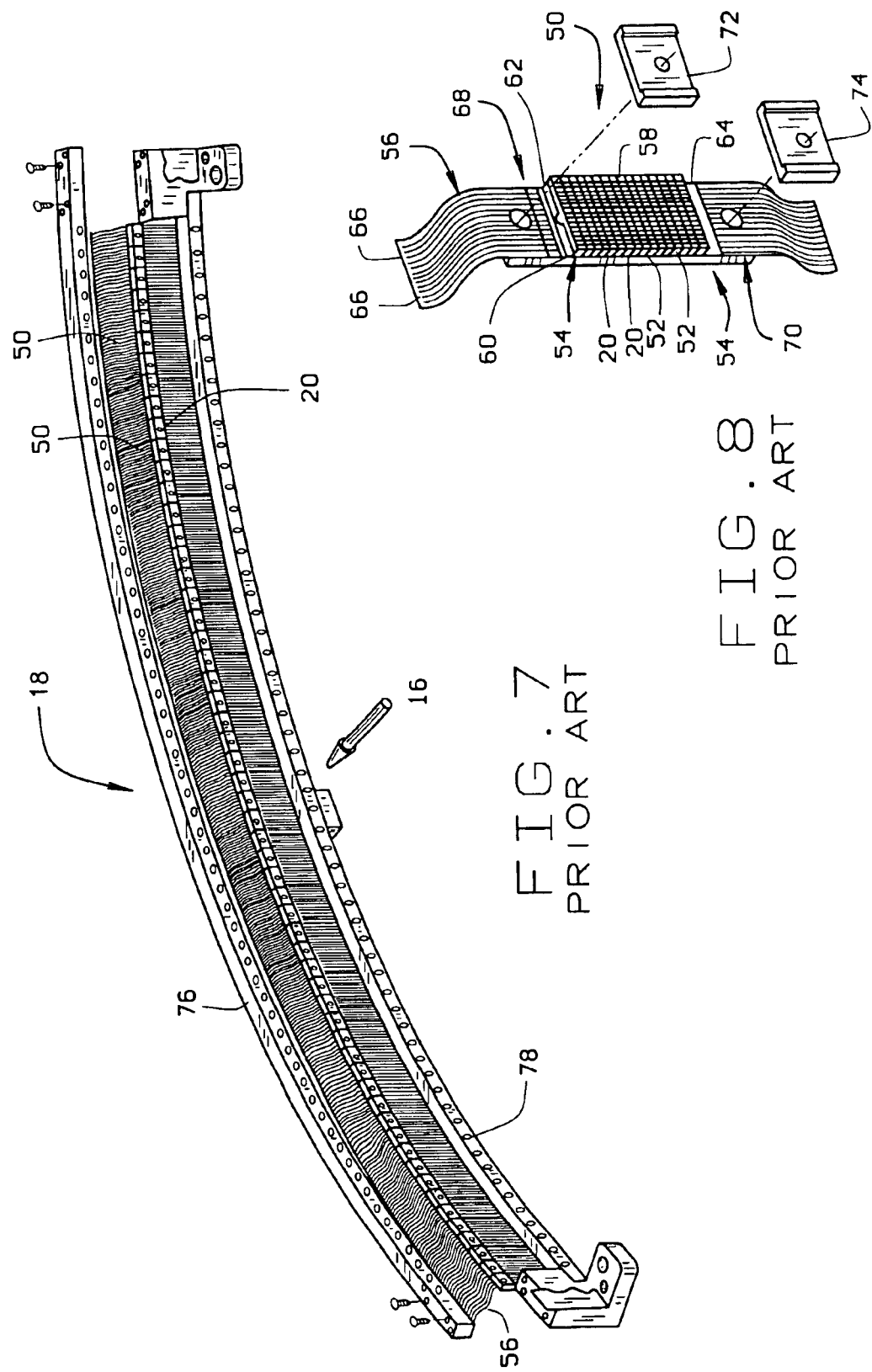
FIG. 7 is a perspective view of a prior art CT system detector array embodiment.
FIG. 8 is a perspective view of a prior art 16×16 detector module of the detector array embodiment of FIG. 7.

Referring to the simplified representation of FIG. 1, a detector array embodiment 82 of the present invention is used in a CT imaging system such as imaging system 10 to image a heart or other organ of patient 22. (FIG. 1 is simplified similarly to FIG. 9.) Detector array 82 replaces, or is provided as original equipment in imaging system 10 of FIG. 5 in place of detector array 18. Detector array embodiment 82 makes advantageous use of the fact that data from only one half of a detector arc rotated around patient 22 is necessary and is equivalent to half scan sampling and image reconstruction. (Each detector cell 20 in half scan sampling receives and measures radiation from at least a 180° arc around patient 22.) Detector array 82 comprises a plurality of half detector segments 84 staggered on left and right sides of centerline 80 (more precisely, on the positive and the negative x-directions from centerline 80). In one CT imaging system 10 embodiment, centerline 80 is defined as an imaginary line of a radiation beam 16 passing through an axis of rotation of gantry 12. Without reference to imaging system 10, a centerline 80 of a staggered detector array 82 can be defined as an imaginary line parallel to the z-direction that bisects detector array 82 in the x-direction. Half detector segments 84 abut one another in regions about centerline 80.

Another embodiment of detector array 82 comprises a plurality of half-detector segments 84 on the same side of centerline 80. (In other words, half-detector segments 84 are not staggered.) However, the staggered embodiment of FIG. 1 provides spaces 86 between half-detector segments. Spaces 86 provide space for prior art detector modules 50 to be used by providing room for rails 88, and 90 to hold modules 50 in array 82. In addition, spaces 86 allow flexible electrical cables 56 to be run out from detector array 82. In half-detector segments 84, modules 50 have four edges, and are each abutted by at most two other modules.

Figure 2:
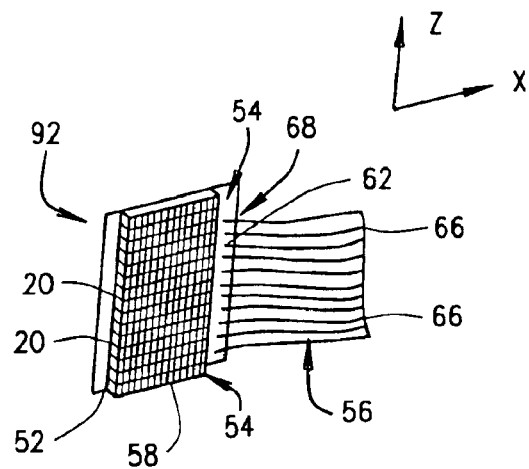
FIG. 2 is a pictorial view of a center detector array module of the detector array embodiment of FIG. 1.

Referring to FIG. 2, center detector module 92 of detector array 82 is constructed differently from prior art modules 20. Because of the limited space available for flexible cables 56 and the presence of adjacent modules in the z-direction, center detector modules 92 are configured so that its flexible electrical cable 56 runs in the x-direction rather than the z-direction, as mounted. To accommodate this construction, electrical output lines 60 (not shown in FIG. 2) and a semiconductor switch 62 are located at one side of detector module 92, in contrast to prior art detector module 50, on which they are located at the top and bottom of the module. In the embodiment of FIG. 2, all signals are handled by one flexible electrical cable 56 extending in one direction and one semiconductor switch 62. This permits the use of detector modules 92 in each half detector segment simply by orienting it in an appropriate direction, as each detector module 92 has butt joints on three other edges. In one embodiment, detector module 92 has a wider electrical cable 56 than detector modules 50 that wraps tightly around the free edge of module 92 so as not to interfere with flexible electrical cables 56 of other modules 50. In one embodiment, cable 56 is shaped with a pre-formed right angle bend. Also in one embodiment, center detector modules 92 at x-extremities of detector array 82 have an extra mounting flange (not shown) for mounting to a collimator rail rather than to a third butt joint.

Center detector modules 92 need not have the same number of detector elements as detector modules 50, and are provided to reduce image center artifacts. Thus, in one embodiment, detector modules 92 straddle centerline 80 in each half detector segment 84 and have sixteen detector cells 20 in the z-direction and fourteen in the x-direction. Also in one embodiment, detector cells 20 are paired (i.e., two are combined by hardwiring to produce a single output) in the x-direction. The two-cell "space" in the x-direction (i.e., fourteen detector cells 20 rather than sixteen) provides space for photodiode 52 signal routing and flexible cable 56 termination. Detector modules 92 having a greater or lesser number of detector cells 20 in the x-direction are used in other embodiments. The number of cells 20 is selected to ensure that the center of the field of view of imaging system 10 is adequately sampled.

As shown in FIG. 1, two types of rails 88, and 90 are used in the construction of detector array 82 and form a portion of a post-patient collimator. Detector modules 50 of detector array 82 are mounted on rails 88 and 90 in a manner similar to that of prior art detector module 18, for example, by screws passing through detector modules 50 into threaded holes in the rails. Rail 88 is unremarkable, and extends across an entire length of a half detector segment 84 in the x-direction. Rails 90 extend across most of the length of a half-detector segment except for a portion at which it abuts a detector module 92 of an adjacent half detector segment 84. At this point, as shown in phantom, it extends beneath center detector module 92 diagonally in one embodiment, and continues as a mounting rail for another half detector segment 86. Center modules 92 are mounted either by adhering them to rails 90 as they run under modules 92. In another embodiment of detector array 82, they are mounted on a free edge (i.e., the edge having flexible cable 56 attached). Thus, rails 88 and 90 are mounted in front of detector modules 50, and rails 90 extend behind center modules 92

In one embodiment, detector modules 50 and 92 of detector array 82 are removable and replaceable.

Post-patient collimator plates 102 are used in one embodiment. Plates 102 are conventional except over center detector modules 92, where each extends the full z-direction thickness of detector 82, i.e., between both rails 88 and over a plurality of center detector modules 92. (Conventional plates 102 extend in the z-direction over only a single detector module 50.) Wires 104 of the post-patient collimator extend transverse to the post-patient collimator plates and present no special construction difficulty. Only a few post patient collimator plates 102 and wires 104 are represented in FIG. 1.

In one embodiment, center modules 92 sit flush over rails 90.

Figure 3:
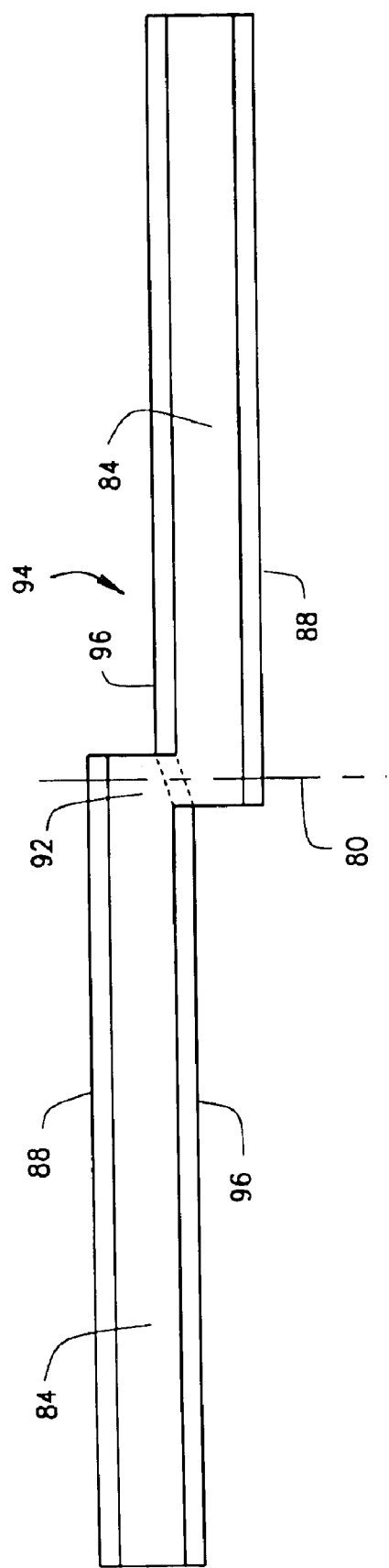
FIG. 3 is a simplified view of a detector array embodiment having a staggered/offset rail joining two detector arrays.

The mounting arrangement shown in FIG. 1 is only exemplary. Moreover, detector array embodiments of the present invention are scalable, for example, in that they can use any number of staggered half-detector segments 84. FIG. 3 represents another detector array embodiment 94 having a slightly different form than detector array embodiment 82 of FIG. 1. This embodiment has only two half detector segments 84. In addition, rail 96 is wide enough to support two center detector modules 92.

One embodiment of cardiac CT imaging system 10 utilizing detector array 82 instead of multislice detector array 18. This embodiment produces a volume of data output similar to that of a standard eight slice imaging system 10 using prior art multislice detector array 18.

Figure 4:
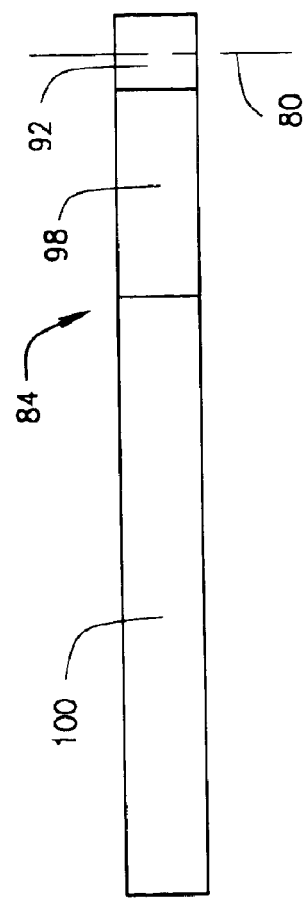
FIG. 4 is a simplified view of one half detector segment of the embodiment of FIG. 1. (Some of the half detector segments are mirror images of the one represented in FIG. 4.)

For example, in one embodiment and referring to FIGS. 2 and 4, detector modules 92 have 16 cells in Z and 7 paired cells in X, for a total of 112 outputs per module. Detector elements 50 in region 98 adjacent to center detector modules 92 have a minimum of 112 detector cells 20 in an x-direction and a 13.04 cm field of view (FOV). A half field of view (FOV) at 541 mm to center of rotation 58 is 6.52 degrees, or about 0.0618 degrees per cell. A total FOV of a heart of patient 22 is therefore 13 cm.

In one embodiment, 7 detector modules 50 each having an array of 16×16 detector cells 20 is used in region 98 adjacent to the center of gantry rotation to provide a 13.04 cm FOV. Detector cells 20 in this embodiment provide 1.25 mm resolution in the z-direction. Cells in the x-direction are paired (i.e., their electrical outputs are connected together) so that there are only 128 distinct outputs per detector module 50. Pairing cells 20 in the x-direction allows a standard detector module 50 to be used throughout detector array 82 with only minor modification. For example, detector modules 50 in one embodiment are hard wired in pairs. In another embodiment, FET arrays 62 and 64 are used in place of hard wiring so that the gain of all pixels can be calibrated. The construction of detector modules 50 is otherwise similar to that of such modules in known multi-slice imaging systems.

Hard wired pairing (or otherwise combining outputs of detector modules 50) reduces the number of DAS 32 data inputs required for processing cardiac images. In addition, summing in the x-direction gives more isotropic voxels in image space when using detector cells 20 dimensioned as described herein. The total number of detector cells 20 in region 98 is thus 7×128=896 cells per array.

A second region 100 of half detector segment 84 supports reconstruction of an entire FOV. However, region 100 is not required to provide cardiac imaging details, and thus can provide much lower detector cell sampling than does region 98. For example, in one embodiment, a 48 cm FOV at 541 mm to isocenter 24 is 26.34 degrees, or 0.0618 degrees per detector cell 20. However, data from cells 20 in each module 50 in region 100 is combined so that each module provides a single output for each row. In other words, all the cells in each module are combined in the x-direction, but the z-direction resolution is still 1.25 mm. Thus, each module 50 provides 16 outputs. In one embodiment, summation of cells in the x-direction is performed within modules 60. In another embodiment, summation is performed in a backplane of DAS 32. In either of these two embodiments, a total of 426 detector cells are to the left of the center of gantry rotation, or 426 cells/16 cells per module=26.63 or twenty-seven total modules 50. Thus, there are twenty modules 50 in region 100, because seven modules 50 are used in region 98. With twenty modules 50 and only sixteen outputs per module 50, there are effectively 320 cell outputs in region 100.

By combining detector cells 20 in the manner described above, detector array 82 provides a relatively higher spatial resolution near centerline 80 and a relatively lesser spatial resolution distal to centerline 80.

A known DAS 32 from an eight-slice CT imaging system includes 48 boards having 128 channels per board, which provides sufficient capability for processing 48×128=6144 detector cells 20. Thus, the known DAS 32 provides sufficient processing capability for 4.63 half detector segments 84 (6144 cells/1328 cells per detector array=4.63 detector arrays). In one embodiment, however, a detector array 82 having five half detector segments 84 is provided for imaging to provide cardiac coverage of 13 cm (X) by 10 cm (Z). Thus, only a few additional DAS 32 boards are required for the additional channels needed. In another embodiment, additional cells 20 in a portion of region 98 adjacent to region 100 are summed to further reduce the amount of data output from the detector array without significantly sacrificing image quality. This embodiment also requires a few additional DAS 32 channels beyond that provided by the known 8 slice CT imaging system. In another embodiment having less cell sampling in regions 100 and/or fewer overlapping cells 20 in regions 98, no additional DAS 32 boards or channels are required.

A modified bowtie can reduce x-ray dosage in the outer low resolution portion of the patient.

In one embodiment of the present invention, to image an organ of patient 22, a volume of the body of patient 22 including the organ of interest is scanned with a computerized imaging system 10 that uses, instead of detector array 18, a detector array 82 of the present invention. Attenuation data is acquired from a plurality of staggered half-detector segments 84 of detector array 82, and an image of the organ of patient 22 is reconstructed using the acquired attenuation data.

It is thus clear that the embodiments described herein provide satisfactory CT cardiac imaging with a minimum number of revolutions of an x-ray source and detector, or, in some embodiments, with only a single revolution. Moreover, the amount of data collected during such a cardiac CT scan is reduced to levels that can be handled by known data acquisition systems with little or no augmentation, without making unacceptable sacrifices in image quality and resolution.

While the invention has been described in terms of various specific embodiments, those skilled in the art will recognize that the invention can be practiced with modification within the spirit and scope of the claims.

What is claimed is:

1. A method for imaging an organ of a patient comprising the steps of:

scanning a volume of a patient's body including an organ of the patient with a computed tomographic (CT) imaging system having a radiation source and a detector array coupled to a rotating gantry, the detector array having a z-direction parallel to an axis of rotation of the gantry and an x-direction transverse to the z-direction;

acquiring attenuation data from a plurality of staggered half detector segments of the detector array, wherein said staggered half detector segments are separated by a gap therebetween, said staggered half detector segments are abutted in regions about a centerline extending in the z-direction, and, in abutting said half detector segments, there are included a first type of detector module having a cable extending a in the z-direction into said gap and a second type of detector module having a cable extending in the x-direction into said gap; and reconstructing an image including the patient's organ using the acquired attenuation data.

2. A method in accordance with claim 1 wherein said step of acquiring attenuation data comprises acquiring attenuation data having different resolutions as a function of position in the x-direction in each said half detector segment.

3. A radiation detector for an imaging system, said radiation detector having a centerline extending in a z-direction and having an x-direction and the z-direction, comprising a plurality of staggered half detector segments abutted in regions about said centerline and separated from one another by a gap, said staggered half detector segments each comprising a plurality of detector modules, and, in abutting said half detector segments, there are included a first type of detector module having a cable extending in the z-direction into said gap and a second type of detector module having a cable extending in the x-direction into said gap.

4. A radiation detector in accordance with claim 3, wherein said cable cables are flexible cables.

5. A radiation detector in accordance with claim 4 wherein said first type of detector module straddles the centerline in each half detector segment.

6. A radiation detector in accordance with claim 5 wherein said flexible cable of said first type of detector module includes a pre-formed right angle bend.

7. A radiation detector in accordance with claim 4 wherein said second type of detector module is included within a plurality of modules configured to provide different numbers of outputs per module as a function of location in the x-direction.

8. A radiation detector in accordance with claim 7 wherein said second type of detector module includes a plurality of detector cells extending in the x-direction and the z-direction, including paired cells.

9. A radiation detector in accordance with claim 3 wherein said cables are flexible cables, and said staggered half detector segments include a set of rails to which said first type of detector module and said second type of detector module are mounted, said rails extending in front of said second type of detector module and behind said first type of detector module.

10. A detector array in accordance with claim 9 and further comprising a set of collimator plates extending in the z-direction, said collimator plates extending over a single said detector module of said second type and extending over a plurality of detector modules of said first type.

11. A detector array in accordance with claim 3 wherein said detector modules are removeable.

12. A computed tomographic (CT) imaging system for imaging an organ of a patient, said CT system comprising:
a rotating gantry having an axis of rotation;
a radiation source configured to rotate with the rotating gantry; and
a multislice detector array having a z-direction parallel to the axis of rotation of the gantry and an x-direction transverse to the z-direction, said multislice detector array configured to rotate with the rotating gantry and configured to acquire attenuation data from a patient between the radiation source and the detector, said detector array comprising a plurality of staggered half-detector segments separated from one another by a gap and abutted in regions about a centerline extending in the z-direction, said half-detector segments configured to provide attenuation data having a relatively higher spatial resolution near a centerline extending in the z-direction of said detector array and a relatively lower spatial resolution distal to said centerline, wherein, in abutting said half-detector segments, there are included a first type of detector module having a cable extending in the z-direction into said gap and a second type of detector module having a cable extending in the x-direction into said gap;
a data acquisition system configured to receive attenuation data from the detector, including the relatively lower spatial attenuation data and the relatively higher spatial resolution attenuation data, and
an image reconstructor configured to utilize the attenuation data to reconstruct an image of the organ, including utilizing the relatively lower spatial resolution data, to thereby reduce artifacts in the image.

13. A CT imaging system in accordance with claim 12 wherein said cables are flexible cables.

14. A CT imaging system in accordance with claim 13 wherein said first type of detector module straddles the centerline in each half detector segment.

15. A CT imaging system in accordance with claim 14 wherein said flexible cable of said first type of detector module includes a pre-formed right angle bend.

16. A CT imaging system in accordance with claim 13 wherein said second type of detector module is included within a plurality of modules configured to provide different numbers of outputs per module as a function of location in the x-direction.

17. A CT imaging system in accordance with claim 16 wherein said second type of detector module includes a plurality of detector cells extending in the x-direction and the z-direction, wherein the plurality of detector cells include paired cells.

18. A CT imaging system in accordance with claim 12 wherein said cables are flexible cables, and said staggered half detector segments include a set of rails to which said first type of detector module and said second type of detector module are mounted, said rails extending in front of said second type of detector module and behind said first type of detector module.

19. A CT imaging system in accordance with claim 18 and further comprising a set of collimator plates extending in the z-direction, said collimator plates including collimator plates extending over a single said detector module of said second type and collimator plates extending over a plurality of detector modules of said first type.

20. A CT imaging system in accordance with claim 12 wherein said first type of detector module is included within a plurality of detector modules that are removable.

* * * * *

UNITED STATES PATENT AND TRADEMARK OFFICE
CERTIFICATE OF CORRECTION

PATENT NO. : 6,873,678 B2
DATED : March 29, 2005
INVENTOR(S) : David M. Hoffman

It is certified that error appears in the above-identified patent and that said Letters Patent is hereby corrected as shown below:

<u>Column 8,</u>
Line 33, after "x-direction" delete "and " and insert therefor -- transverse to --.

Signed and Sealed this

Twenty-third Day of August, 2005

JON W. DUDAS
*Director of the United States Patent and Trademark Office*